United States Patent [19]

Englert et al.

[11] Patent Number: 5,043,344

[45] Date of Patent: Aug. 27, 1991

[54] UNSATURATED N-BENZOPYRANYLLACTAMS

[75] Inventors: Heinrich C. Englert, Hofheim am Taunus; Dieter Mania; Bernward Schölkens, both of Kelkheim; Roland Utz, Messel, all of Fed. Rep. of Germany

[73] Assignee: Hoechst Aktiengesellschaft, Frankfurt am Main, Fed. Rep. of Germany

[21] Appl. No.: 330,042

[22] Filed: Mar. 29, 1989

[30] Foreign Application Priority Data

Mar. 31, 1988 [DE] Fed. Rep. of Germany ....... 3811017

[51] Int. Cl.$^5$ .................. C07D 405/14; A61K 31/44
[52] U.S. Cl. .................. 514/337; 514/422; 546/269; 548/525
[58] Field of Search ............ 546/269; 414/337

[56] References Cited

FOREIGN PATENT DOCUMENTS 0076075 4/1983 European Pat. Off. .
0091748 10/1983 European Pat. Off. .
0120428 10/1984 European Pat. Off. .

OTHER PUBLICATIONS

Merk 9th Ed., p. 1047.

Primary Examiner—Jane T. Fan
Attorney, Agent, or Firm—Finnegan, Henderson, Farabow, Garrett, and Dunner

[57] ABSTRACT

Compounds I

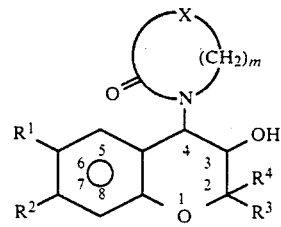

where $R^1$ is H, alkyl, alkoxy, CO alkyl, COOH, carboxyalkyl, $CONR_2$, CN, $NO_2$, alkylsulfi(o)nyl, arylsulfi(i)nyl; $R^2$ is H, OH, alkoxy, alkyl or alkylcarbonyl, $R^3/R^4$ are alkyl, m is zero or one and X is $-CR^6=CR^7-(-CR^8=CR^9)$ ($R^6 R^9$ are H or alkyl), where n is zero or 1, are described. They are active antihypertensives and spasmolytics for the bladder, intestine, gall bladder, uterus, trachea and ureter.

6 Claims, No Drawings

UNSATURATED N-BENZOPYRANYLLACTAMS

DESCRIPTION

The invention relates to unsaturated 3,4-dihydro-2H-benzo[b]pyrans of the formula I

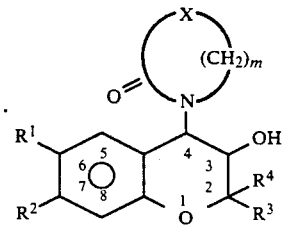

in which:

$R^1$ denotes H, $(C_1-C_4)$alkyl, $(C_1-C_4)$alkoxy, halogen, trifluoromethyl, CO-$(C_1-C_4)$alkyl, CO-Ar, COOH, carboxyalkyl$(C_1-C_4)$

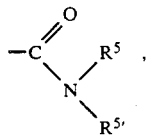

in which $R^5$ and $R^{5'}$ are identical or different and stand for H or $(C_1-C_2)$alkyl, C≡N, $NO_{2l}$, $(C_1-C_4)$alkyl$SO_r$- or Ar$SO_r$-, in which r stands for 0, 1 or 2 and Ar stands for an aromatic or heteroaromatic system which is unsubstituted or substituted by 1 to 3 identical or different radicals from the group comprising $(C_1-C_2)$alkyl, halogen, C≡N, $NO_2$, $CF_3$, COOH or carboxyalkyl$(C_1-C_2)$, $R^2$ denotes H, OH, $(C_1-C_2)$alkoxy, $(C_1-C_2)$alkyl or $(C_1-C_2)$alkylcarbonyl, $R^3$ and $R^4$ (identical or different) denote $(C_1-C_4)$alkyl, X denotes a chain with the following structure

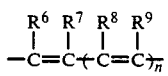

in which $R^6$, $R^7$, $R^8$ and $R^9$ are identical or different and stand for H, $(C_1-C_4)$alkyl, halogen or $NO_2$, m denotes zero or 1 and n denotes zero or 1, m and n always being different, but where, for compounds where m is zero, $R^1$ only denotes CO-Ar or Ar$SO_r$.

In the compounds of the above formula I, when m is zero and n is 1, the compound will have the formula Ia

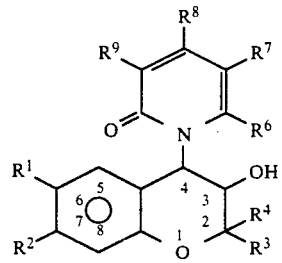

in which $R^1$, $R^2$, $R^3$, $R^4$, $R^6$, $R^7$, $R^8$ and $R^9$ are as defined above.

An aromatic system Ar is preferably understood as phenyl, naphehyl or biphenylyl, and a 5- to 6-membered hetero-aromatic system Ar is preferably a radical of a 5- or 6-membered 0-, N- and/or S-heterocyclic ring, in particular furyl, thienyl, isothiazolyl, oxazolyl, isoxazolyl, pyrazolyl, imidazolyl, thiazolyl, pyridyl, pyrazinyl, pyrimidinyl, pyridazinyl and thiazinyl.

Halogen is understood as F, Cl, Br or I, preferably F, Cl or Br.

The C atoms 3 and 4 of the 3,4-dihydro-2H-benzo[b]-pyran system (also abbreviated to "chroman system" below) of the formula I are asymmetrically substituted. The invention thereby relates to only those compounds which have opposite configurations at these centers, that is to say a "trans orientation" of the substituents on these carbon atoms.

If one of the substituents $R^1$, $R^2$, $R^3$, $R^4$ and X contains asymmetry centers or if $R^3$ and $R^4$ are different (and thus produce an asymmetric carbon atom), the invention relates both to compounds with centers with the S-con-figuration and to compounds with centers with the R-con-figuration.

The compounds can be present as optical isomers, as diastereomers, as racemates or as mixtures thereof.

Preferred compounds of the formula I are those in which $R^1$ stands for halogen, C≡N, $NO_2$ or phenylsulfonyl, which is unsubstituted or substituted as defined above, $R^2$ denotes H or $(C_1-C_2)$alkoxy, $R^3$ and $R^4$ are as defined above and X and m have the meaning described above.

Particularly preferred compounds of the formula I are those in which $R^1$ stands for halogen, CN, $NO_2$ or phenyl-sulfonyl, which is unsubstituted or monosubstituted by $(C_1-C_2)$alkyl, cyano, $(C_1-C_2)$alkoxy or halogen, $R^2$ denotes H or $(C_1-C_2)$ alkoxy, $R^3$ and $R^4$ are as defined above, m is 1, n is zero and the substituents $R^6$ and $R^7$ in X can be identical or different and stand for H or $(C_1-C_4)$alkyl.

Compounds of the formula I which are likewise furthermore preferred are those in which $R^1$ stands for benzoyl and phenylsulfonyl, which is unsubstituted or mono-substituted by $(C_1-C_2)$alkyl, cyano, $(C_1-C_2)$alkoxy or halogen, $R^2$ denotes H or $(C_1-C_2)$alkoxy, $R^3$ and $R^4$ are as defined above, m is zero, n is 1, one of the substituents $R^6$ to $R^9$ in X stands for $CH_3$, Cl, CN or COOH and the remaining substituents stand for H.

Particularly preferred compounds of the formula I are those in which $R^1$ stands for C≡N or phenylsulfonyl, which is unsubstituted or monosubstituted by $(C_1-C_2)$alkoxy, $R^2$ denotes H or $(C_1-C_2)$alkoxy, $R^3$ and $R^4$ are as defined above, m is 1, n is zero and the substituents $R^6$ and $R^7$ in X can be identical or different and stand for H or $(C_1-C_4)$alkyl.

Especially preferred compounds of the formula I, however, are those in which $R^1$ stands for phenylsulfonyl, which is unsubstituted or monosubstituted by $(C_1-C_2)$-alkoxy, $R^2$ denotes H or $(C_1-C_2)$alkoxy, $R^3$ and $R^4$ are as defined above, m is zero, n is 1, one of the substituents $R^6$ to $R^9$ in X stands for $CH_3$ or Cl and the remaining substituents stand for H.

EP Offenlegungsschrift 273,262 proposes chromans which are substituted in the phenyl ring by 1,2-dihydro-2-oxo-pyrid-1-yl.

Compounds which are structurally very close to the compounds according to the invention are described in J. Med. Chem. 1986, 29, 2194-2201. They are summarized therein under the following general formulae:

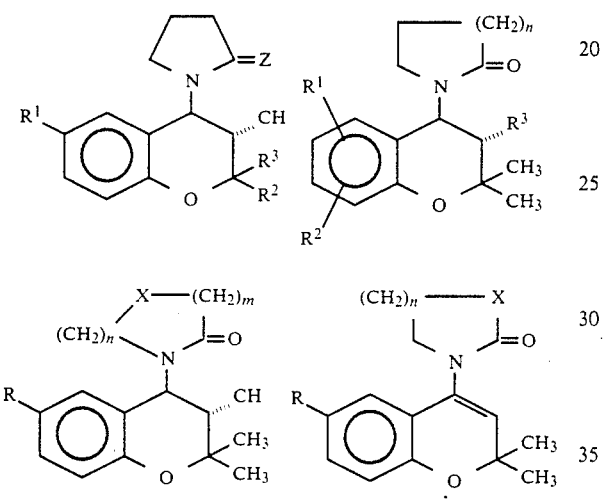

in which $R^1$, $R^2$, $R^3$, Z, n, m and R have the meanings given therein. A large proportion of these compounds has also been the subject of various patent applications, and there may be mentioned here EP 0,107,423, EP 0,120,427, EP 0,076,075 and EP 0,120,428.

In particular, those compounds which carry a CN or an $NO_2$ group in the 6-position of the 3,4-dihydro-2H-benzopyran system have been described in the above-mentioned literature reference as being particularly active, and particular importance is attributed especially to (+)-6-cyano-3,4-dihydro-2,2-dimethyl-trans-4-(2-oxo-1-pyrrolidinyl)-2H-benzo[b]pyran-3-ol.

Surprisingly, the introduction of unsaturated cyclic amides into the 4-position of the chroman system has led to novel active compounds with useful pharmacological properties. They have an antihypertensive action and/or have a relaxing action on organs such as the bladder, intestine, gall bladder, uterus, trachea and ureter. The compounds I according to the invention can thus be used as antihypertensives, as coronary therapeutics or as agents for the treatment of cardiac insufficiency. However, they can also be used as spasmolytics for the abovementioned organs. They can thereby be used either in human or in veterinary medicine.

The invention furthermore relates to a process for the preparation of the compounds I, which comprises a) reacting compounds of the formula II

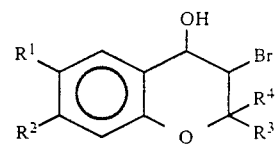

in which $R^1$ to $R^4$ are as defined above, with lactams of the formula III

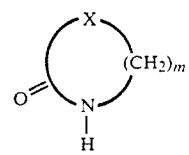

or
b) reacting compounds of the formula IV

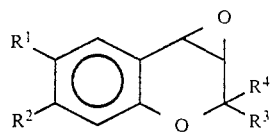

p10 in which $R^1$ to $R^4$ are as defined above, with lactams of the formula III

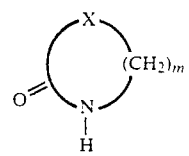

or
c) reacting compounds of the formula IV

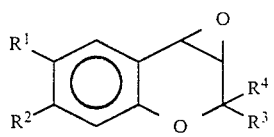

in which $R^1$ to $R^4$ are as defined above, with the N-silyllactams V

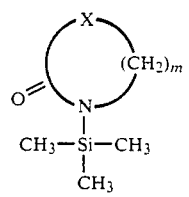

or
d) reacting compounds of the formula IV

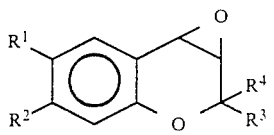

in which $R^1$ to $R^4$ are as defined above, with the o-silyl derivatives VI

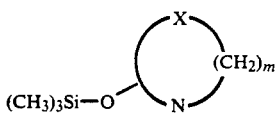
VI or e) acylating compounds of the formula VII

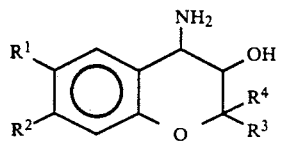
VII in which $R^1$ to $R^4$ are as defined above, to give the compounds VIII

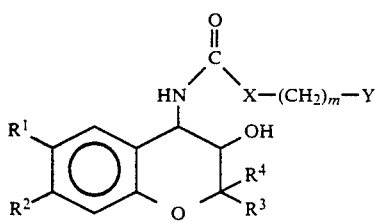
VIII in which Y is a leaving group, such as, for example, chlorine or bromine, and $R^1$ to $R^4$ are as defined above, and cyclizing these to give the compounds I, or f) oxidizing compounds of the formula IX

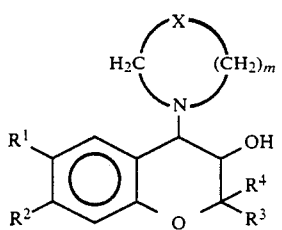
IX in which $R^1$ to $R^4$ are as defined above, to give the compounds I.

If the compounds I are prepared by methods a) or b), this is effected by reacting the compounds II or IV with the lactams III in a suitable solvent, preferably in dipolar aprotic solvents, such as, for example, dimethyl sulfoxide or tetrahydrofuran, preferably under the action of a base, such as, for example, sodium hydride, potassium hydride, K tert.-butylate, Na 2-methyl-2-butylate, lithium bis-(trimethylsilyl)-amide or similar bases which are known to be suitable for N-alkylation of lactams. The reaction temperature can thereby be varied within a wide range; the reaction is preferably carried out between 0° C. and room temperature, or at temperatures which can be slightly above room temperature.

Compounds which can be prepared by methods a) or b) only with difficulty can often be rendered very readily accessible by processes c) and d).

In these, the compounds IV and the compounds V or VI are stirred together in the presence of a desilylating agent, such as potassium tert.-butylate or tetrabutylammonium fluoride, in a dipolar aprotic solvent, but preferably in tetrahydrofuran. It is also possible to carry out the reaction without a solvent, in which case the liquid silyl compounds V and VI are usually employed in excess in order to keep the batch stirrable. The temperature can thereby be varied within wide limits. Thus, in many cases, the compounds I according to the invention are already obtained just at room temperature, and in other cases they are obtained only after heating to 120° C. or even higher.

Lactams of the formula III are known in many cases, or they can easily be prepared by methods which are known from the literature.

The silyl compounds V and VI can easily be prepared by methods which are known from the literature from the lactams of the formula III, for example by heating with 1,1,1,3,3,3-hexamethyldisilazane.

Compounds II and IV are novel. They can be prepared, for example, by the following synthesis route.

Compounds of the formula X

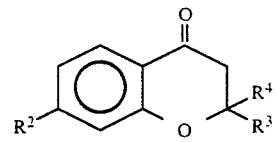
X in which $R^2$, $R^3$ and $R^4$ are as defined above, are reacted with acid chlorides $ArSO_2Cl$ by Friedel-Crafts acylation in a manner which is known per se to give compounds of the formula XI

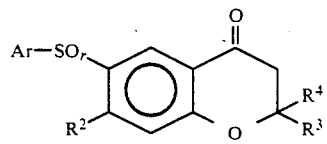
XI in which $R^2$, $R^3$, $R^4$ and Ar are as defined above.

Compounds of the formula X in which $R^2$, $R^3$ and $R^4$ are as defined above are reacted with $NaNO_3$ or N-bromosuccinimide in concentrated sulfuric acid in a manner which is known per se to give compounds of the formula XII and XIII

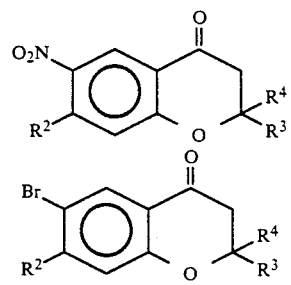
XII

XIII

The compounds of the formula XII can be converted into the corresponding halides of the formula XIV in a manner which is known per se.

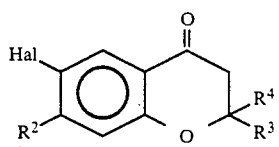
XIV

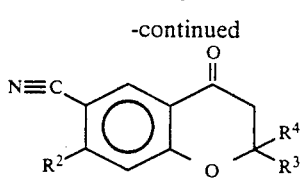

The compounds of the formula XIII can be converted into the corresponding nitriles of the formula XV in a manner which is known per se.

The compounds XI, XII, XIII, XIV and XV are converted, by reduction under standard conditions, for example by NaBH₄ in methanol or ethanol, into the compounds of the formula XVI

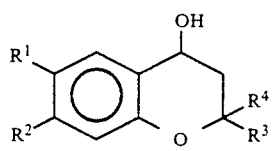

in which $R^1$, $R^2$, $R^3$ and $R^4$ are as defined above.

The compounds of the formula XVI are then subjected to removal of water, for example by pyridine/phosphorus oxychloride or p-toluenesulfonic acid/toluene, compounds XVII being formed:

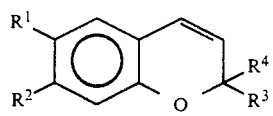

An important expedient process for introducing a very wide variety of radicals $R^1$ into compounds of the formula II and IV involves metallating compounds of the formula XVII in which $R^1$ denotes Br and $R^2$, $R^3$ and $R^4$ are as defined above, in the 6-position at $-78°$ C. in THF using 2 equivalents of tert.-butyllithium, and reacting the aryllithium compounds with a large number of electrophiles in a manner which is known per se.

Compounds of the formula XVII in which $R^1$ denotes Br and $R^2$, $R^3$ and $R^4$ are as defined above can be prepared very simply by reducing compounds of the formula X in which $R^2$, $R^3$ and $R^4$ are as defined above, analogously to the preparation of the compounds XVI. In this way, compounds of the formula XVI in which $R^1$ denotes H and $R^2$, $R^3$ and $R^4$ are as defined above are obtained. The introduction of $R^1 = Br$ into the compound of the formula XVI in which $R1 = H$ and $R^2$, $R^3$ and $R^4$ are as defined above succeeds using N-bromosuccinimide in glacial acetic acid.

In this way, compounds of the formula XVI in which $R^1$ is Br and $R^2$, $R^3$ and $R^4$ are as defined above are obtained; these compounds can be converted as described above into the compounds of the formula XVII in which $R^1 = Br$ and $R^2$, $R^3$ and $R^4$ are as defined above.

Compounds XVII can now easily be converted into the epoxides IV or the bromohydrins II by standard methods.

If $R^2$ denotes OH in this reaction sequence, protective groups, such as, for example, the acetyl or methyl group, may be necessary for the OH group. These are split off again by customary methods at suitable stages, preferably after carrying out the reactions described in processes a), b), c), d), e) and f).

In some cases, chromenes of the formula XVII are prepared in a manner which is known per se by thermally induced cyclization of the corresponding propargyl ethers XVIII

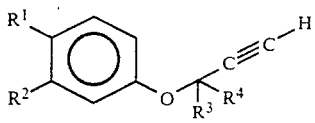

These can in turn be prepared in a manner which is known per se from the phenols XIX and the propargyl chlorides XX

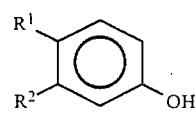

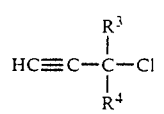

Processes e) and f) can be particularly advantageously used if enantiomerically pure end products I are desired.

In contrast to the compounds I, the compounds VII and IX are basic and are thus capable of salt formation with organic acids. They can be obtained in enantiomerically pure form in a manner which is known per se by crystallization with a suitable optically uniform acid, such as, for example, (+)-mandelic acid or (+)-lactic acid, and can be converted into enantiomerically pure end products I by processes e) and f).

However, enantiomerically pure end products I can also be resolved out of racemic end products I by customary methods of resolution of racemates, such as, for example, chromatographic separation using chiral phases or derivatization of the racemic products with optically uniform acid derivatives (ester formation via the 3-hydroxy group of the chroman system) or with optically uniform isocyanates (carbamate formation via the 3-hydroxy group). The diastereomeric isocyanates or esters thereby obtained can be separated by customary methods (crystallization or chromatography) and converted into the optically uniform end compounds, the optically active auxiliary group on the 3-OH function being split off. Resolution of the diastereomeric 3-menthoxyacetates has proved particularly advantageous here.

EXAMPLE 1 trans-3,4-Dihydro-4-(1,2-dihydro-2-oxo-pyrid-1-yl)-2,2-dimethyl-6-(phenylsulfonyl)-2H-benzo [b]pyran-3-ol.

3.16 g (10 mmol) of tetrabutylammonium fluoride trihydrate are added under argon and with cooling to a solution of 3.16 g (10 mmol) of 3,4-dihydro-2,2-dimethyl-3,4-epoxy-6-(phenylsulfonyl)-2H-benzo[b]pyran in 4 ml of absolute THF and 3.35 g (20 mmol) of 2-trimethylsilyloxypyridine, and the mixture is stirred at room temperature for 60 hours. The mixture is diluted with water and extracted three times with ethyl acetate. The organic phase is washed with water and saturated sodium chloride solution, dried over sodium sulfate, filtered and evaporated in vacuo. The oily residue is chromatographed on silica gel using ethyl acetate/cyclohexane 9:1.

The amorphous white substance is dried in a high vacuum.

$C_{22}H_{21}NO_5S$ (429.47) cal. C 61.52;H 5.40;N 3.26; $H_2O$ found C 61.8;H 5.1;N 3.2;

Preparation of the starting material:
3,4-Dihydro-2,2-dimethyl-3,4-epoxy-6-(phenylsulfonyl)2H-benzo[b]pyran is obtained from trans-3-bromo-3,4-di-hydro-2,2-dimethyl-6-(phenylsulfonyl)-2H-benzo[b]pyran-4-ol using NaH in DMSO.

Melting point: 103°–105° C. trans-3-Bromo-3,4-dihydro-2,2-dimethyl-6-(phenylsulfonyl)2H-benzo[b]pyran-4-ol is obtained from 2,2-dimethyl-6-phenylsulfonyl-2H-chromene and N-bromosuccinimide in a 9:1 dimethyl sulfoxide/$H_2O$ mixture.

Melting point: 126°0 C.

2,2-Dimethyl-6-phenylsulfonyl-2H-chromene having the melting point 70°–71° C. was prepared by known methods from 4-phenylsulfonylphenyl 1,1-dimethylpropargyl ether. This ether was likewise obtained in a known manner from 4-phenylsulfonylphenol and 3-methyl-3-chlorobutyne.

EXAMPLE 2 trans-4-(5-Chloro-1,2-dihydro-2-oxo-pyrid-1-yl)-3,4-dihydro-6-(phenylsulfonyl)-2H-benzo[b]pyran-3-ol 3.16 g (10 mmol) of 3,4-dihydro-2,2-dimethyl-3,4-epoxy-6-(phenylsulfonyl)-2H-benzo[b]pyran are dissolved in 4 ml of absolute THF, and 4.00 g (20 mmol) of 5-chloro-2-tri-methylsilyloxy-pyridine are added under argon. 3.16 g (20 mmol) of tetrabutylammonium fluoride trihydrate in solid form are then added with cooling, and the mixture is stirred at room temperature for about 60 hours. The mixture is worked up by adding water and extracting three times with ethyl acetate. The organic phase is washed with water and concentrated aqueous sodium chloride solution. After drying over magnesium sulfate, filtration and evaporation of the solvent in vacuo, a white foam which can be crystallized in butyl acetate is obtained.

White crystals of melting point 218°–220° C. are obtained.

$C_{22}H_{22}ClNO_5S$ (445.90) calc. C 59.26;H 4.52;N 3.14; found C 59.1; H 4.5; N 3.1 ;

Preparation of the starting material:
3,4-Dihydro-2,2-dimethyl-3,4-epoxy-6-(phenylsulfonyl)2H-benzo[b]pyran, see under Example 1.

5-Chloro-2-trimethylsilyloxy-pyridine is obtained by heating 5-chloro-2-hydroxy-pyridine with 1,1,1,3,3,3-hexamethyldisilazane at 100° to 110° C. and subsequently distilling the product in vacuo.

EXAMPLE 3 trans-3,4-Dihydro-4-(1,2-dihydro-2-oxo-pyrid-1-yl)-2,2-dimethyl-6-(2-methoxyphenylsulfonyl) -2H-benzo[b]pyran-3-ol 3.5 g (0.0082 mol) of trans-3-bromo-3,4-dihydro-2,2-di-methyl-6-(2-methoxyphenylsulfonyl)-2H benzo[b]-pyran-4-ol are added to a suspension of 0.6 g of NaH (80% in oil) (0.0246 mol) and 3.1 g of 2-hydroxypyridine in 50 ml of dimethyl sulfoxide. The mixture is warmed to 60° C. and stirred for 3 hours. The mixture is poured into ice water, and the white precipitate is filtered off with suction and dried in air. Chromatography on silica gel using methanol/ethyl acetate 1:10 gives the product as a white, amorphous powder.

$C_{23}H_{23}NO_6S$ (441.49) calc. C 62.5; H 5.25; N 3.1; found C 61.8; H 5.3; N 2.9 ;

Preparation of the starting material:

trans-3-Bromo-3,4-dihydro-2,2-dimethyl-6-(2-methoxyphenyl-sulfonyl)-2H-benzo[b]pyran-4-ol is prepared analogously to Example 1.

EXAMPLE 4 trans-3,4-Dihydro-4-(1,2-dihydro-2-oxo-pyrid-1-yl)-2,2-dimethyl-7-methoxy-6-phenylsulfonyl -2H-benzo[b]pyran-3-ol Preparation analogously to Example 3. Purification is carried out by chromatography on silica gel using toluene/ethyl acetate 4:1. White crystals of melting point 228°–29° C.

Preparation of the starting material:
trans-3-Bromo-3,4-dihydro-2,2-dimethyl-7-methoxy-6-phenyl-sulfonyl-2H-benzo[b]pyran-4-ol is obtained from 2,2-dimethyl-7-methoxy-6-phenylsulfonyl-2H-chroman and N-bromosuccinimide in a 9:1 dimethyl sulfoxide/$H_2O$ mixture.

Melting point: 202°–203° C.

2,2-Dimethyl-7-methoxy-6-phenylsulfonyl-2H-chromene is obtained from 2,2-dimethyl-4-hydroxy-7-methoxy-6-phenylsulfonylchromene using pyridine/phosphorus oxychloride in benzene.

Melting point: 140°–41° C.

2,2-Dimethyl-4-hydroxy-7-methoxy-6-phenylsulfonyl-chroman is obtained from 2,2-dimethyl-7-methoxy-6-phenylsulfonyl-chroman-4-one using sodium borohydride in methanol.

Melting point: 146°–147° C.

2,2-Dimethyl-7-methoxy-6-phenylsulfonyl-chroman-4-one is obtained from phenylsulfonyl chloride, 2,2-dimethyl-7-methoxychroman-4-one and aluminum chloride in methylene chloride.

Melting point: 223°–25° C.

EXAMPLE 5 trans-3,4-Dihydro-2,2-dimethyl-4-(3-ethyl-4-methyl-2-oxo-3-pyrrolin-1-yl)-6-6-(phenylsulfonyl)-2H-benzo[b]-pyran -3-ol 3.80 g (12.02 mmol) of 3,4-dihydro-2,2-dimethyl-3,4-epoxy-6-(phenylsulfonyl)-2H-benzo[b]pyran and 1.50 g (12.02 mmol) of 3-ethyl-4-methyl-2-oxo-3-pyrroline are dissolved in 5 ml of absolute THF, and 12.02 ml of lithium bis-(tri-methylsilyl)-amide (1 molar solution in THF) are injected under argon. The mixture is stirred at room temperature for 72 hours and then diluted with water. The viscous oil which is deposited is crystallized twice in butyl acetate. White crystals of melting point 128°–135° C. are obtained.

$C_{24}H_{27}NO_5S$ (441.52) calc. C 63.98;H 6.26;N 3.11; found C 63.8;H 6.2;N 3.1 ;

Preparation of the starting material:
3,4-Dihydro-2,2-dimethyl-3,4-epoxy-6-(phenylsulfonyl)-2H-benzo[p]pyran, see under Example 1.

-3-Ethyl-4-methyl-2-oxo-3-pyrroline is known from the literature.

EXAMPLE 6 trans-3,4-Dihydro-2,2-dimethyl-4-(3,4-dimethyl-2-oxo-3-pyrrolin-1-yl)-6-(phenylsulfonyl) -2H-benzo[b]-pyran-3-ol The compound can be prepared analogously to Example 5. After crystallization in ethyl acetate/cyclohexane, white crystals of melting point 191°–193° C. are obtained.

C₂₃H₂₅NO₅S (436.50) calc. C 63.28;H 5.87;N 3.21;
found C 63.3;H 6.0;N 3.2;
Preparation of the starting material:
3,4-Dihydro-2,2-dimethyl-3,4-epoxy-6-(phenylsulfonyl)-2H-benzo[b]pyran, see under Example 1.
3,4-Dimethyl-2-oxo-3-pyrroline is known from the literature.

EXAMPLE 7 trans-6-Cyano-3,4-dihydro-2,2-dimethyl-4-(3-ethyl-4-methyl-2-oxo-3-pyrrolin-1-yl) -2H-benzo[b]pyran-3-ol 2.4 g (0.08 mol) of 80% NaH are introduced into a solution of 14.4 g (0.072 mol) of trans-3-bromo-6-cyano-3,4-dihydro-2,2-dimethyl-2H-benzo[b]pyran -4-ol in 200 ml of DMSO. The mixture is stirred for one hour at 20° C., and 3.6 g (0.12 mol) of 80% NaH and 15 g (0.12 mol) of 3-ethyl-4-methyl-2-oxo-3-pyrroline are introduced. The reaction mixture is stirred at 40° C. for three hours and then introduced into ice water, and the product is filtered off with suction, dried and chromatographed on a silica gel column using methylene chloride/methanol (95 : 5). The product obtained in this way crystallizes from a little ethanol.

Crystals of melting point 207°–208° C.
C₁₉H₂₂N₂O₄ (326,41) calc. C 69.92;H 6.80;N 8.58;
found C 70.0;H 6.7;N 8.6 ;
Preparation of the starting material:
trans-3-Bromo-6-cyano-3,4-dihydro-2,2-dimethyl-2H-benzo[b]pyran-4-ol and 3-ethyl-4-methyl-2-oxo-3-pyrroline are known from the literature.

EXAMPLE 8 trans-6-Cyano-3,4-dihydro-2,2-dimethyl-4-(3,4-dimethyl-2-oxo-3-pyrrolin-1-yl)-2H -benzo[b]pyran-3-ol The compound can be prepared analogously to Example 5. After crystallization in water/ethanol, crystals of melting point 217°–219° C. are obtained.
C₁₈H₂₀N₂O₃ (312.35) calc. C 69.21;H 6.45;N 8.92;
found C 68.9;H 6.2;N 8.9;
Preparation of the starting material:
6-Cyano-3,4-dihydro-2,2-dimethyl-3,4-epoxy-2H-benzo[b]pyran and 2-trimethylsilyloxy-pyridine are known from the literature.

EXAMPLE 9 trans-3,4-Dihydro-4-(1,2-dihydro-5-nitro-2-oxo-pyrid-1-yl)-2,2-dimethyl-6-phenylsulfonyl -2H-benzo[b]pyran-3-ol 4.00 g (12.6 mmol) of 3,4-dihydro-2,2-dimethyl-3,4-epoxy-6-(phenylsulfonyl)-2H-benzo[b]pyran and 1.77 g (12.6 mmol) of 2-hydroxy-5-nitropyridine are suspended in a little absolute THF, and 16.7 ml (12.6 mmol) of a 1 M solution of lithium bis-trimethylsilylamide are added dropwise under argon with stirring and ice cooling. The mixture is stirred at room temperature for a further 72 hours, hydrolyzed and extracted three times with ethyl acetate. The combined organic extracts are washed with water and saturated sodium chloride solution and dried over sodium sulfate. The solvent is evaporated in vacuo and the residue is chromatographed on silica gel (ethyl acetate/ cyclohexane 1:1). The compound can be crystallized in ethyl acetate.
Melting point 212–214° C.
C₂₂H₂ON₂O₇S (456.48) calc. C 57.8;H 4.4;N 6.1;
found C 57.7;H 4.2;N 6.2 ;

Preparation of the starting material, see under Example 1.

EXAMPLE 10 trans-3,4-Dihydro-4-(1,2-dihydro-2-oxo-pyrid-1-yl)-2,2-dimethyl-6-(2-trifluoro methyl-benzoyl)-2H-benzo[b]pyran-3-ol 5.15 g (12 mmol) of trans-3-bromo-3,4-dihydro-2,2-dimethyl-6-(2-trifluoromethyl-benzoyl)-2H -benzo[b]pyran-4-ol are suspended in 6.02 g (36 mmol) of 2-trimethylsilyloxypyridine under argon, and 9.46 g (30 mmol) of tetrabutylammoniumfluoride trihydrate are added with stirring. The mixture is stirred at 55° C. for about 15 hours, hydrolyzed and extracted three times with ethyl acetate. The combined ethyl acetate extracts are washed with water and saturated sodium chloride solution and dried using sodium sulfate, and the solvent is evaporated in vacuo. The foamy residue is triturated with diisopropyl ether and filtered off with suction. The crystals are dried in a high vacuum.
Melting point: 184°–186° C.
C₂₄H₂₀F₃NO₄ (443.43) calc. C 65.0 ;H 4.5;N 3.16;
found C 65.3; H 4.6;N 3.1;
Preparation of the starting material:
The reaction of 2-hydroxyacetophenone with acetone in the presence of pyrrolidine analogously to Synthesis 886, 1978 gives 2,2-dimethyl-4-chromanone of melting point 80°–85° C. 2,2-Dimethyl-4-hydroxy-chroman (oil) is obtained from 2,2-dimethyl-4-chromanone by reduction using sodium borohydride in ethanol.
6-Bromo-2,2-dimethyl-4-hydroxy-chroman of melting point 97°–99° C. is obtained by reacting 2,2-dimethyl-4-hydroxychroman with N-bromosuccinimide in glacial acetic acid.
6-Bromo-2,2-dimethyl-2H-chroman, which is an oil, is obtained from 6-bromo-2,2-dimethyl-4-hydroxychroman by azeotropic removal of water in toluene with addition of catalytic amounts of p-toluenesulfonic acid.
6-Bromo-2,2-dimethyl-2H-chromene is metallated at −78° C. using 2 equivalents of tert.-butyllithium and subsequently reacted with 2-trifluoromethylbenzaldehyde to give 2,2-dimethyl-6-(2-trifluoromethyl-hydroxybenzyl)-2H-chromene which is produced as an oil.
2,2-Dimethyl-6-(2-trifluoromethyl-hydroxybenzyl)-2H-chromene is oxidized using pyridinium-chlorochromate in methylene chloride to give 2,2-dimethyl-6-(2-trifluoro-methyl-benzoyl)-2H-chroman, from which trans-3-bromo-3,4-dihydro-2,2-dimethyl-6-(2-trifluoromethyl-benzoyl)-2H-benzo[b]pyran -4-ol, which is an oil, is obtained as described in the preceding examples.

EXAMPLE 11

In an analogous manner to that described under Example 10, trans-3,4-dihydro-4-(1,2-dihydro-2-oxo-pyrid-1-yl)-2,2-dimethyl-6-(2-fluoro-benzoyl)-2H -benzo[b]pyran3-ol of melting point 241°–243° C. is obtained.
C₂₃H₂₀FNO₄ (393.93) calc. C 70.21;H 5.12;N 3.56;
found C 70.1 ;H5.2 ;N 3.5.;
We claim:
1. An unsaturated 3,4-dihydro-2H-benzo-pyran of the formula Ia

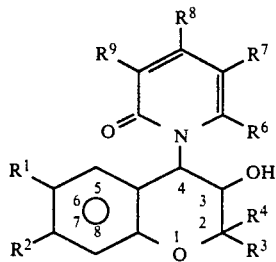

in which

R$^1$ is phenylsulfonyl or benzoyl,

R$^2$ is H or (C$_1$-C$_2$) alkoxy,

R$^3$ and R$^4$ are identical or different (C$_1$-C$_4$) alkyl, and one of the substituents R$^6$ to R$^9$ is CH$_3$ and the other three substituents are H.

2. An unsaturated 3,4-dihydro-2H-benzo-pyran of the formula Ia

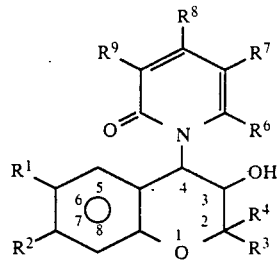

in which
R$^1$ is phenylsulfonyl or benzoyl in which the phenyl nucleus is unsubstituted or monosubstituted by (C$_1$-C$_2$) alkoxy,
R$^2$ is H or (C$_1$-C$_2$) alkoxy,
R$^3$ and R$^4$ are identical or different (C$_1$-C$_4$)alkyl, and one of the substituents R$^6$ to R$^9$ is Cl or CH$_3$ and the other three substituents are H.

3. A pharmaceutical composition for reducing the blood pressure which comprises an effective amount of a compound of the formula Ia as claimed in claim 1 together with a pharmaceutically acceptable vehicle.

4. A method for reducing the blood pressure which comprises administering to a host an effective amount of a compound of the formula Ia as claimed in claim 1.

5. A pharmaceutical composition for reducing the blood pressure which comprises an effective amount of a compound of the formula Ia as claimed in claim 2 together with a pharmaceutically acceptable vehicle.

6. A method for reducing the blood pressure which comprises administering to a host an effective amount of a compound of the formula Ia as claimed in claim 2.

* * * * *